US006440464B1

(12) United States Patent
Hsia et al.

(10) Patent No.: US 6,440,464 B1
(45) Date of Patent: *Aug. 27, 2002

(54) NUTRITIVE COMPOSITION FOR CARDIOVASCULAR HEALTH CONTAINING FISH OIL, GARLIC, RUTIN, CAPSAICIN, SELENIUM, VITAMINS AND JUICE CONCENTRATES

(75) Inventors: Houn Simon Hsia, Foothill Ranch; David Fan, Mission Veijo, both of CA (US)

(73) Assignee: Viva Life Science, Costa Mesa, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/845,155

(22) Filed: Apr. 21, 1997

Related U.S. Application Data

(63) Continuation-in-part of application No. 08/661,088, filed on Jun. 10, 1996, now abandoned.

(51) Int. Cl.[7] ................................................ A61K 35/78
(52) U.S. Cl. ...................... 424/725; 424/754; 424/760; 424/554; 424/523; 426/599; 426/601; 426/602; 426/648
(58) Field of Search ................................. 424/523, 554, 424/195.1, 725, 754, 760; 426/73, 599, 601, 602, 648, 641

(56) References Cited

U.S. PATENT DOCUMENTS 4,963,380 A * 10/1990 Schroeder ................ 426/330.3
4,976,969 A * 12/1990 Grossman ................ 424/195.1

FOREIGN PATENT DOCUMENTS

| EP | 0232501 | * 12/1986 |
| FR | 2720647 | * 6/1994 |
| WO | 94/02166 | * 2/1994 |

OTHER PUBLICATIONS

Schrauzer et al., Trace Substances in Environmental Health XIII, vol. 13, 1979, pp. 64–67.*

Simon et al., Archives of Internal Medicine, 1994, vol. 154, pp. 2283–2296.*

The Merck Index, p. 1195–1196, 1983.*

Kirschmann et al. "Nutrition Almanac", 1984, Mc.Graw Hill, pages 60–64, 86–87, 96, –97, 99, 104–105.*

* cited by examiner

Primary Examiner—Irene Marx
(74) Attorney, Agent, or Firm—Lyon & Lyon LLP

(57) ABSTRACT

The present invention relates to the use of nutritional supplement compositions to overcome nutritional deficiencies typically associated with the normal mammalian diet. The compositions of the present invention are obtained by combining fish oil, garlic powder, rutin, capsaicin, vitamin A, vitamin C, vitamin E, selenium, and one or more juice concentrates.

22 Claims, No Drawings

NUTRITIVE COMPOSITION FOR CARDIOVASCULAR HEALTH CONTAINING FISH OIL, GARLIC, RUTIN, CAPSAICIN, SELENIUM, VITAMINS AND JUICE CONCENTRATES

CROSS-REFERENCE TO RELATED APPLICATION

This is a continuation-in-part of co-pending non-provisional application Ser. No. 08/661,088, filed Jun. 10, 1996 now abandoned.

BACKGROUND OF THE INVENTION

1. Field of the Invention

The present invention provides a novel nutritive compositions, and more specifically to nutritive compositions containing fish oil, garlic, rutin, capsaicin, vitamin A (beta carotene), vitamin E, vitamin C, selenium and selected juice concentrates, for reducing the levels of triglycerides, cholesterol, and low density lipoprotein (LDL) in human blood serum, and for lowering the blood pressure, and for increasing the levels of high density lipoprotein (HDL) in human blood serum.

2. Background of the Invention

In the last few years, scientific literature has provided strong evidence for a bona fide link between micronutrient compositions (such as vitamins, minerals, fish oils, and plant extracts) and cardiovascular disease. For humans of high risk for cardiovascular diseases, realizing an appreciable reduction in the levels of high cholesterol, triglycerides, low density lipoprotein (LDL) in their blood serum is known to be important for reducing the risk of cardiac diseases. It is also known that effecting an increase in the levels of high density lipoprotein (HDL) also provides a significant decrease to the risk of cardiac diseases.

Cardiovascular disease resulting from the buildup of arterial plaque is known to be a leading cause of illness and death in humans. Arterial plaque is caused by precipitous material formed chiefly of oxidized low density lipoprotein (O-LDL). The buildup of plaque in the form of O-LDL in the arteries is understood to be a factor in ischemic heart disease. Free radical oxidants, many of which come from naturally occurring sources such as sun exposure, metabolism of certain nutrients, exercise, or are otherwise often observed in persons suffering from diabetes and high blood pressure, act to oxidize LDL into its deleterious form, O-LDL. Free radical "scavengers" such as vitamins A, E, C, and selenium are believed to react with these oxidants and render them incapable of oxidation. The inhibitory action of these antioxidants thus inhibits the formation of O-LDL, thereby lowering the levels of arterial plaque deposits in blood vessels. In contrast, the presence of high density lipoprotein (HDL) in the body is understood to have beneficial health effects. Specifically, HDL is known to be a more soluble form of lipoprotein, hence its presence does not significantly contribute to the formation of arterial plaque. In addition, it is known that HDL is able to absorb plaque material and may thus directly reduce the amount of arterial plaque.

3. Description of Prior Art

Essential fatty acids (EFAs) are naturally occurring unsaturated fatty acids with a chain length of 18, 20, or 22 carbon atoms. These EFAs cannot be synthesized by the body, hence, dietary intake of EFAs is required. Two fatty acids which fall within the family of EFAs are eicosapantaenoic acid (EPA) and docosahexaenoic acid (DHA), both of which are commonly found in fish oils. Epidemiological observations indicate that fish oils reduce platelet aggregation and serum triglycerides which may reduce the risk of myocardial infarction, hypertension, atherosclerosis, and certain types of cancer. [Gerster, H., Internat. J. Vit. Nutr. Res., 65:3–20 (1994)]. Specifically, it has been shown that EPA and DHA derived from fish oils play important structural roles in membranes of most cells, and influence the fluidity of the cell membranes as expressed by decreased whole-blood viscosity and increased erythrocyte flexibility and deformability [Gerster, cited above]. In addition, EFAs such as EPA and DHA are known precursors of eicosanoids—a class of compounds which includes prostanoids such as prostaglandins and thromboxanes, leukotrienes, and hydroxy fatty acids. Eicosanoids are known are known to affect platelet aggregation, permeability and tone of the blood vessel walls, blood pressure, and inflammatory immune reactions. [Gerster, cited above].

Fish oil dietary supplementation is known to have other beneficial health effects. Glycogen storage disease is an inherited disorder, and is often complicated by severe hyperlipoproteinemia and hypercholesterolemia, which increase the risk of premature atherosclerosis and cardiovascular diseases. It has been reported that patients suffering from glycogen storage disease that received 10 grams of fish oil for 3 months experienced a significant decrease in levels of triglycerides in the blood serum (−49%) and cholesterol levels in the blood serum (−23%), and a reduction in LDL levels in the blood serum (−40%), and a significant increase in HDL levels in the blood serum (+30%). [Levy, E., et al., I. Am. J. Clin. Nutr., 57:922–29 (1993)].

Garlic powder has been proposed to have a number of valuable benefits to the human body as a preventative against cardiovascular diseases. For example, daily ingestion of garlic leads to reduced levels of lipids in human blood serum, increased fibrinolysis and tissue plasminogen activator (t-PA) activity, and decreased plasma fibrogen viscosity, each of which may lessen the likelihood of cardiovascular disease. [Brosche, T. et al., British J. Clin. Practice, Supp. 69:12–19 (1990); Kiesewetter H. et al., British J. Clin. Practice, Supp. 69:24–29 (1990)]. In addition, the daily ingestion of garlic is known to reduce the total levels of cholesterol and triglycerides in human serum, as well as reduce blood pressure peripheral vasodilation. [Auer, W. et al., British J. Clin. Practice, Supp. 69:3–6 (1990)].

Flavonoids are secondary metabolites which are found in edible plants and foodstuffs derived from plants. Flavonoids are widely recognized as having antiallergic, anti-inflammatory, antiviral, antiproliferative and anticarcinogenic activities. [Manach, C., et al. J. Nutr., 125:1911–22 (1995)]. Among flavonoids, flavonols occur most abundantly in plants as possess most of these biological properties. [Manach, cited above]. Flavonols naturally occur as O-glycides, typically having a sugar moiety bound at the C-3 position. Rutin is the principal glycoside form of quercetin, the most abundant flavonol in fruits and vegetables.

Capsaicin is a prominent chemical entity in plants of the Capsicum genus, which include chili peppers, red pepper, and paprika. Capsaicin is actually a class of compounds of branched- and straight-chain alkyl vanillylamides. The antimicrobial and analgesic properties of capsaicin have been known for centuries. In addition, capsaicin-containing products have been used to treat rheumatoid arthritis, osteoarthritis, diabetic neuropathy, postherpetic neuralgia, postmastectomy pain syndrome, cluster headache, and reflex sympathetic syndrome. [Cordell, G. and Araujo, O., *Ann. Pharm.*, 27:330–36 (1993)].

Certain vitamins and minerals, antioxidants, and plant extracts are generally known to have beneficial health effects. For example, several beneficial aspects of antioxidants have been known for many years. Antioxidants are chemicals that react with free radicals, such as hydroxy radical, to protect certain biological systems. The removal of free radicals from the body has been suggested to increase human longevity—specifically, the presence of antioxidants including superoxide dismutase (SOD), carotenoids, alpha-tocopherol, and uric acid is suggested to have a positive correlation with resistance to spontaneous autoxidation of tissues and oxidative damage to DNA in mammals [Cutler, R., *Am. J. Clin. Nutr.*, 53:373S–9S (1991)]. Antioxidants are also known to limit destruction of healing brain tissue by free radicals as shown by the method for resuscitating the brain using vitamins such as A, E and C or selenium [See, Klatz et al., U.S. Pat. No. 5,149,321 and PCT application PCT/US92/06681].

In addition to their antioxidant activity, vitamins A, C, and E are well known to have other beneficial health effects. For example, vitamin E is known to help maintain proper blood sugar levels. As another example, vitamin C is known to play an integral role in the integrity of connective and structural tissues in the body. Vitamin A is known to play a role in maintaining good vision as well as in growth and development. Hence, an adequate supply of these vitamins is essential in maintaining optimum health. The use of vitamins A, E, C and selenium has been proposed as a means to inhibit or prevent collagen cross-linking in human skin when used in combination with certain active peptides [See, Geoffrey et al., PCT application WO 90/06102].

Although compositions used to reduce the risks of cardiovascular disease are known, the present invention comprises a novel combination of fish oil, garlic, rutin, capsaicin, vitamin A, vitamin C, vitamin E and selenium, and juice concentrates, which achieve this purpose. As such, there remains a need in the art for novel compositions like those of the present invention which may be used to treat or prevent cardiovascular disease and disorders.

SUMMARY OF THE INVENTION

The present invention relates to the use of nutritional supplement compositions to overcome nutritional deficiencies typically associated with the normal mammalian diet. The compositions of the present invention are obtained by combining fish oil, garlic powder, rutin, capsaicin, vitamin A, vitamin C, vitamin E, selenium, and one or more juice concentrates. Specifically, the present invention relates to the daily administration of fish oil, garlic powder, rutin, capsaicin, vitamin A, vitamin C, vitamin E, selenium, and one or more juice concentrates, in separate preparations, or in preparations that contain combinations of the ingredients, or preferably, in a single lozenge.

It is therefore an object of the invention to provide nutritious and safe compositions for human consumption as dietary supplements that contain fish oil, garlic powder, rutin, capsaicin, vitamin A, vitamin C, vitamin E, selenium, and juice concentrates.

It is another object to provide novel compositions which will increase the levels of HDL in human blood serum.

It is a further object of the invention to provide compositions which will decrease levels of O-LDL in human blood serum.

It is still another object of the invention to provide compositions which will reduce the levels of cholesterol and triglycerides in human blood serum.

It is yet another object of the present invention to provide compositions that will lower the blood pressure of the human system.

The increase of HDL and the reduction of cholesterol, triglycerides, blood pressure and O-LDL should act to reduce the risk of heart disease in humans. Therefore, it is the prime object of the present invention to provide for the reduction of the risk of cardiovascular disease by daily administration of the compositions of the invention.

DETAILED DESCRIPTION OF THE INVENTION

Daily doses of the compositions of the present invention are aimed at reducing the rate of occurrence of heart disease and are comprised of: (1) fish oil; (2) garlic powder; (3) rutin; (4) capsaicin; (5) vitamin A; (6) vitamin C; (7) vitamin E; (8) selenium; and, (9) one or more juice concentrates.

Throughout the description of the compositions of the present invention, the term "dosage" will refer to a daily dosage—i.e., the total dosage administered in a single day. A dosage, therefore, may comprise one or more dosage forms and one or more administrations of such dosage forms in a single day.

The fish oil component of the compositions of the present invention may be available from commercial sources. [Arista, Pharmachem]. EPA and DHA are the active moieties of the fish oil component. The fish oil component of the present invention comprises EPA in the amount of about 250 mg to about 3500 mg, and most preferably about 3000 mg. The remainder of the fish oil component comprises from about 150 mg to about 2500 mg of DHA, and preferably about 2000 mg of DHA. The total weight of the fish oil component of the present invention is from about 500 mg to about 15,000 mg, and preferably about 5,000 mg to about 10,000 mg per dosage.

The garlic powder used in the compositions of the present invention may be obtained from commercially available sources. [Extracts, Ashland, Pure-Gar]. In addition, it is preferable to use a deodorized and aged form of garlic powder. A pharmaceutically acceptable form of garlic powder used in the compositions of the present invention comprises, by weight, from about 100 mg to about 7,000 mg, and more preferably about 1,750 mg to about 6,500 mg, and most preferably about 3,500 mg of deodorized and aged garlic powder per dosage.

The rutin which is employed in compositions of the present invention may also be obtained from commercially available sources. [Westco Chemical, Freeman Industries, Inc.]. The rutin comprises, by weight, from about 10 mg to about 1500 mg, and most preferably about 1000 mg per dosage.

Capsaicin which is used in the compositions of the present inventions may be commercially obtained. [AllChem, Good Hope Botanicals]. The capsaicin component of the present invention comprises, by weight, from about 20 mg to about 1500 mg, and most preferably about 1000 mg of capsaicin per dosage.

A compendial grade of vitamin A can be employed as the vitamin A component of the present composition. The vitamin A component comprises, by weight, about 1,000 IU to about 20,000 IU of vitamin A, preferably about 2,000 IU to about 15,000 IU of vitamin A and most preferably about 2,500 IU to about 10,000 IU of vitamin A per dose.

A compendial grade of vitamin C can be employed as the vitamin C component of the present composition. The vitamin C component comprises, by weight, about 50 mg to about 4,000 mg of vitamin C, preferably about 150 mg to about 3,000 mg of vitamin C and most preferably about 175 mg to about 2,000 mg of vitamin C per dose.

A compendial grade of vitamin E can also be employed as the vitamin E component of the present composition. The vitamin E component comprises about 50 IU to about 1,000 IU of vitamin E, preferably about 75 IU to about 925 IU of vitamin E, and most preferably about 125 IU to about 425 IU of vitamin E per dose.

A compendial grade of organoselenium or selenium salt can be incorporated as the selenium component of the present invention. Alternatively, selenium yeast may be used as the source of selenium for the compositions of the present invention. Such forms of selenium yeast are commercially available. [Universal Foods Corp.]. The selenium component of the present invention comprises, by weight, about 20 $\mu$g to about 400 $\mu$g of selenium, preferably about 55 $\mu$g to about 300 $\mu$g, and most preferably about 150 $\mu$g to about 250 $\mu$g of selenium per dose.

The total weight of the juice concentrates component in the preferred embodiment of the compositions of the present invention is about 1,000 mg to about 7,500 mg, and most preferably about 2,000 mg to about 6,000 mg per dose.

A suitable composition consistent with the present invention comprises juice concentrates having a concentration of at least 10 times that of the native juice in the unconcentrated form, and preferably about 15 times more concentrated, and most preferably about 20 times more concentrated than the unconcentrated juice. In concentrated form, the juice concentrates are substantially anhydrous, and are generally in powder form.

When present, a form of acorn squash concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of alfalfa juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of apple juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of apricot juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of artichoke juice concentrate suitable for use to supplement the human diet that can be used in present invention comprises about 0.5% to about 20% of the weight of the total juice concentrate component of the present invention, and most preferably about 2% of the weight of the juice concentrate component of the present invention.

When present, a form of avocado juice concentrate suitable for use to supplement the human diet that can be used in the present invention comprises about 0.5% to about 20% of the weight of the total juice concentrate component of the present invention, and most preferably about 1% of the weight of the juice concentrate component of the present invention.

When present, a form of banana juice concentrate suitable for use to supplement the human diet that can be used in the present invention comprises about 0.5% to about 20% of the weight of the total juice concentrate component of the present invention, and most preferably about 1% of the weight of the juice concentrate component of the present invention.

When present, a form of bell pepper juice concentrate suitable for use to supplement the human diet that can be used in the present invention comprises about 0.5% to about 20% of the weight of the total juice concentrate component of the present invention, and most preferably about 1% of the weight of the juice concentrate component of the present invention.

When present, a form of broccoli juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of brussels sprout juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of cabbage juice concentrate suitable for use to supplement the human diet that can be used in the present invention comprises about 1% to about 20% of the weight of the total juice concentrate component of the present invention, and most preferably about 2% of the weight of the juice concentrate component of the present invention.

When present, a form of cantaloupe juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of carrot juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of cauliflower juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of celery juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of cherry juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of collard greens juice concentrate suitable for use to supplement the human diet that can be used in the present invention comprises about 1% to about 20% of the weight of the total juice concentrate component of the present invention, and most preferably about 2% of the weight of the juice concentrate component of the present invention.

When present, a form of grape juice concentrate suitable for use to supplement the human diet that can be used in the present invention comprises about 0.5% to about 20% of the weight of the total juice concentrate component of the present invention, and most preferably about 2% of the weight of the juice concentrate component of the present invention.

When present, a form of grapefruit juice concentrate suitable for use to supplement the human diet that can be used in the present invention comprises about 0.5% to about 20% of the weight of the total juice concentrate component of the present invention, and most preferably about 2% of the weight of the juice concentrate component of the present invention.

When present, a form of green barley juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of green leek juice concentrate suitable for use to supplement the human diet that can be used in the present invention comprises about 0.5% to about 20% of the weight of the total juice concentrate component of the present invention, and most preferably about 2% of the weight of the juice concentrate component of the present invention.

When present, a form of green lettuce juice concentrate suitable for use to supplement the human diet that can be used in the present invention comprises about 0.5% to about 20% of the weight of the total juice concentrate component of the present invention, and most preferably about 1% of the weight of the juice concentrate component of the present invention.

When present, a form of kale juice concentrate suitable for use to supplement the human diet that can be used in the present invention comprises about 0.5% to about 20% of the weight of the total juice concentrate component of the present invention, and most preferably about 1% of the weight of the juice concentrate component of the present invention.

When present, a form of kiwi fruit juice concentrate suitable for use to supplement the human diet that can be used in the present invention comprises about 0.5% to about 20% of the weight of the total juice concentrate component of the present invention, and most preferably about 1% of the weight of the juice concentrate component of the present invention.

When present, a form of kohlrabi juice concentrate suitable for use to supplement the human diet that can be used in the present invention comprises about 0.5% to about 20% of the weight of the total juice concentrate component of the present invention, and most preferably about 1% of the weight of the juice concentrate component of the present invention.

When present, a form of leek juice concentrate suitable for use to supplement the human diet that can be used in the present invention comprises about 0.5% to about 20% of the weight of the total juice concentrate component of the present invention, and most preferably about 1% of the weight of the juice concentrate component of the present invention.

When present, a form of lettuce juice concentrate suitable for use to supplement the human diet that can be used in the present invention comprises about 0.5% to about 20% of the weight of the total juice concentrate component of the present invention, and most preferably about 1% of the weight of the juice concentrate component of the present invention.

When present, a form of onion juice concentrate suitable for use to supplement the human diet that can be used in the present invention comprises about 0.5% to about 20% of the weight of the total juice concentrate component of the present invention, and most preferably about 5% of the weight of the juice concentrate component of the present invention.

When present, a form of orange juice concentrate suitable for use to supplement the human diet that can be used in the present invention comprises about 0.5% to about 20% of the weight of the total juice concentrate component of the present invention, and most preferably about 5% of the weight of the juice concentrate component of the present invention.

When present, a form of papaya juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of parsley juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of potato juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of prune juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of savoy cabbage juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of spinach juice concentrate suitable for use to supplement the human diet that can be used in the present invention comprises about 1% to about 20% of the weight of the total juice concentrate component of the present invention, more preferably about 7.5% to about 15%, and most preferably about 8% to about 12% of the weight of the juice concentrate component of the present invention.

When present, a form of strawberry juice concentrate suitable for use to supplement the human diet that can be used in the present invention comprises about 0.5% to about 20% of the weight of the total juice concentrate component of the present invention, and most preferably about 2% of the weight of the juice concentrate component of the present invention.

When present, a form of sweet potato juice concentrate suitable for use to supplement the human diet that can be used in the present invention comprises about 0.5% to about 20% of the weight of the total juice concentrate component of the present invention, and most preferably about 2% of the weight of the juice concentrate component of the present invention.

When present, a form of swiss chard juice concentrate suitable for use to supplement the human diet that can be used in the present invention comprises about 0.5% to about 20% of the weight of the total juice concentrate component of the present invention, and most preferably about 2% of the weight of the juice concentrate component of the present invention.

When present, a form of tomato juice concentrate suitable for use to supplement the human diet that can be used in the present invention comprises about 1% to about 20% of the weight of the total juice concentrate component of the present invention, and most preferably about 3% of the weight of the juice concentrate component of the present invention.

These preparations may be made by conventional methods. To prepare the compositions of the invention, the above-described fish oil, garlic powder, rutin, and capsaicin components are combined in one preparation as the active ingredient in intimate admixture with a suitable carrier according to conventional compounding techniques. To prepare the compositions of the invention, the above-described vitamin A, vitamin E, vitamin C, selenium, and juice concentrate components are combined in one preparation as the active ingredient in intimate admixture with a suitable carrier according to conventional compounding techniques. The two preparations are then co-administered.

Suitable carriers may take a wide variety of forms depending upon the form of preparation desired for administration, e.g., oral, sublingual, nasal, or parenteral.

In preparing the compositions in oral dosage form, any of the usual pharmaceutical media may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, gelatin capsules, pills, and tablets). Gelatin capsule are a preferred oral dosage form. Lozenges, and controlled release forms may also be used. Because of their ease in administration, lozenges, tablets, pills, and capsules represent the most advantageous oral dosage unit form, in which case solid pharmaceutical carriers are obviously employed. If desired, tablets may be sugar coated or enteric coated by standard techniques.

Examples of these additional inactive components which provide for easier oral administration include but are not limited to lemon bioflavonoids [Botanical International, Freeman], parsley powder, bee's wax, lecithin, gelatin, purified water, and glycerin. These compounds may be used in creating the lozenges of the novel nutritional supplements.

For parenteral products, the carrier will usually comprise sterile water, although other ingredients may be included, e.g., to aid solubility or for preservation purposes. Injectable suspensions may also be prepared, in which case appropriate liquid carriers, suspending agents, and the like may be employed.

A preferred method for using the present invention is for the user to ingest, daily from about 5 to 10 lozenges of the fish oil, garlic, rutin, and capsaicin preparation together with from about 1 to 4 lozenges of the vitamin A, vitamin E, vitamin C, selenium, and juice concentrate preparation.

The following examples illustrate the preferred embodiments of the present invention. These examples are illustrative only, and do not purport to limit the invention in any fashion.

EXAMPLE 1

The following example provides a preferred composition of the present invention. The composition is provided as two separate preparations: lozenge A (fish oil, garlic, capsaicin, and rutin preparation), and lozenge B (vitamin A, vitamin E, vitamin C, selenium, and juice concentrate preparation). The proper daily dosage is 5 to 10 of lozenge A and 1 to 4 of lozenge B.

| LOZENGE A | |
| --- | --- |
| Ingredient | Weight |
| fish oil* | 570 mg |
| garlic powder | 194 mg |
| rutin | 11 mg |
| capsaicin | 21 mg |
| lemon bioflavonoids | 11 mg |
| parsley powder | 38 mg |

-continued

| Ingredient | Approximate Amount |
|---|---|
| d-alpha tocopherol | 5 mg |
| bee's wax | 75 mg |
| lecithin | 75 mg |
| gelatin | 255 mg |
| purified water | 10 mg |
| glycerin | 170 mg |

LOZENGE B

| Ingredient | Approximate Amount |
|---|---|
| Vitamin A (from beta carotene) | 2,500 IU |
| Vitamin C | 250 mg |
| Vitamin E | 50 IU |
| Selenium | 50 µg |
| Barley juice concentrate (approx. 20–1) | 120 mg |
| Spinach juice concentrate (approx. 20–1) | 125 mg |
| Alfalfa juice concentrate (approx. 20–1) | 145 mg |
| Parsley juice concentrate (approx. 20–1) | 135 mg |
| Artichoke juice concentrate (approx. 20–1) | 135 mg |
| Carrot juice concentrate (approx. 20–1) | 130 mg |
| Cabbage juice concentrate (approx. 20–1) | 130 mg |
| Strawberry juice concentrate (approx. 20–1) | 130 mg |
| Papaya juice concentrate (approx. 20–1) | 130 mg |

*Fish oil is in the form of 300:200 of EPA:DHA

EXAMPLE 2

| Ingredient | Approximate Amount |
|---|---|
| Vitamin A (from beta carotene) | 2,500 IU |
| Vitamin C | 250 mg |
| Vitamin E | 50 IU |
| Sodium selenate | 50 µg |
| Barley juice concentrate (approx. 20–1) | 140 mg |
| Spinach juice concentrate (approx. 20–1) | 105 mg |
| Alfalfa juice concentrate (approx. 20–1) | 145 mg |
| Parsley juice concentrate (approx. 20–1) | 105 mg |
| Artichoke juice concentrate (approx. 20–1) | 115 mg |
| Carrot juice concentrate (approx. 20–1) | 145 mg |
| Cabbage juice concentrate (approx. 20–1) | 120 mg |
| Strawberry juice concentrate (approx. 20–1) | 140 mg |
| Papaya juice concentrate (approx. 20–1) | 130 mg |
| Apple juice concentrate | 68 mg |
| glycerin | 340 mg |
| fish oil* | 980 mg |
| garlic powder | 350 mg |
| rutin | 28 mg |
| capsaicin | 22 mg |
| lemon bioflavonoids | 12 mg |
| parsley powder | 31 mg |
| d-alpha tocopherol | 5 mg |

*Fish oil is in the form of 300:200 of EPA:DHA.

EXAMPLE 3

The ingredients of Example 3 are to be combined to form two lozenges. The daily dosage of these lozenges is from 5 to 10 daily.

| Ingredient | Approximate Amount |
|---|---|
| fish oil* | 340 mg |
| garlic powder | 144 mg |
| rutin | 13 mg |
| capsaicin | 22 mg |
| lemon bioflavonoids | 12 mg |
| parsley powder | 31 mg |
| d-alpha tocopherol | 5 mg |
| bee's wax | 75 mg |
| lecithin | 75 mg |
| d-alpha tocopheryl acetate | 48 mg |
| 700 IU/g [Eastman Chem. Co.] | |
| Selenium Yeast (1,000 ppm Se) [Universal Foods Corp.] | 27 mg |
| Beta carotene (167,000 IU/g) [BASF Corp.] | 29 mg |
| Riboflavin [Takeda U.S.A., Inc.] | 0.9 mg |
| Ascorbic Acid (USP grade) [Hoffmann-La Roche, Inc.] | 200 mg |
| Citrus Pectin Cellulose [Stauber Performance Ingredients Inc.] | 6.3 mg |
| Microcrystalline Cellulose [FMC Corp.] | 85 mg |
| Di-Calcium phosphate [Brown Chemical Co. Inc.] | 8.7 mg |
| Magnesium Stearate [Stauber Performance Ingredients, Inc.] | 1.5 mg |
| Freeze dried alfalfa powder [Freeze-dry products USA, Inc.] | 5.3 mg |
| Freeze dried apple powder [Freeze-dry products USA, Inc.] | 6.3 mg |
| Freeze dried artichoke powder [Freeze-dry products USA, Inc.] | 7.2 mg |
| Freeze dried onion powder [Freeze-dry products USA, Inc.] | 7.9 mg |
| Freeze dried banana powder [Freeze-dry products USA, Inc.] | 16 mg |
| Freeze dried strawberry powder [Freeze-dry products USA, Inc.] | 17 mg |
| Freeze dried collard greens powder [Freeze-dry products USA, Inc.] | 12 mg |
| Freeze dried papaya powder [Freeze-dry products USA, Inc.] | 13 mg |
| Freeze dried green lettuce powder [Freeze-dry products USA, Inc.] | 19 mg |
| Freeze dried tomato powder [Freeze-dry products USA, Inc.] | 5 mg |
| Freeze dried broccoli powder [Freeze-dry products USA, Inc.] | 7.9 mg |
| Freeze dried cabbage powder [Freeze-dry products USA, Inc.] | 8.2 mg |
| Freeze dried cantaloupe powder [Freeze-dry products USA, Inc.] | 10.1 mg |
| Freeze dried cherry powder [Freeze-dry products USA, Inc.] | 7 mg |
| Freeze dried kale powder [Freeze-dry products USA, Inc.] | 9 mg |
| Freeze dried kiwi fruit powder [Freeze-dry products USA, Inc.] | 8 mg |
| Freeze dried kohlrabi powder [Freeze-dry products USA, Inc.] | 7 mg |
| Freeze dried grape powder [Freeze-dry products USA, Inc.] | 6 mg |
| Freeze dried grapefruit powder [Freeze-dry products USA, Inc.] | 7 mg |
| Freeze dried leek powder [Freeze-dry products USA, Inc.] | 8 mg |
| Freeze dried brussels sprout powder [Freeze-dry products USA, Inc.] | 7 mg |
| Freeze dried orange powder [Freeze-dry products USA, Inc.] | 6 mg |
| Freeze dried parsley powder [Freeze-dry products USA, Inc.] | 6 mg |
| Freeze dried potato powder [Freeze-dry products USA, Inc.] | 8 mg |
| Freeze dried bell pepper powder [Freeze-dry products USA, Inc.] | 5 mg |
| Freeze dried prune powder | 5 mg |

-continued

| Ingredient | Approximate Amount |
|---|---|
| [Freeze-dry products USA, Inc.] Freeze dried carrot powder | 12 mg |
| [Freeze-dry products USA, Inc.] Freeze dried Swiss chard powder | 13 mg |
| [Freeze-dry products USA, Inc.] Freeze dried spinach powder | 5 mg |
| [Freeze-dry products USA, Inc.] Freeze dried apricot powder | 13 mg |
| [Freeze-dry products USA, Inc.] Freeze dried avocado powder | 5 mg |
| [Freeze-dry products USA, Inc.] Freeze dried acorn squash powder | 10 mg |
| [Freeze-dry products USA, Inc.] Freeze dried savoy cabbage powder | 11 mg |
| [Freeze-dry products USA, Inc.] Freeze dried celery powder | 12 mg |
| [Freeze-dry products USA, Inc.] Freeze dried cauliflower powder | 15 mg |
| [Freeze-dry products USA, Inc.] Freeze dried sweet potato powder [Freeze-dry products USA, Inc.] | 14 mg |

*Fish oil is in the form of 300:200 of EPA:DHA.

EXAMPLE 4

The ingredients of Example 4 are to be combined to form 2 lozenges. The daily dosage of these lozenges is from 2 to 6 daily.

| Ingredient | Approximate Amount |
|---|---|
| fish oil* | 580 mg |
| garlic powder | 184 mg |
| rutin | 13 mg |
| capsaicin | 22 mg |
| lemon bioflavonoids | 12 mg |
| parsley powder | 31 mg |
| d-alpha tocopherol | 5 mg |
| bee's wax | 75 mg |
| lecithin | 75 mg |
| d-alpha tocopheryl acetate 700 IU/g [Eastman Chem. Co.] | 250 mg |
| Selenium Yeast (1,000 ppm Se) [Universal Foods Corp.] | 130 mg |
| Beta carotene (167,000 IU/g) [BASF Corp.] | 125 mg |
| Riboflavin [Takeda U.S.A., Inc.] | 400 mg |
| Ascorbic Acid (USP grade) [Hoffmann-La Roche, Inc.] | 600 mg |
| Citrus Pectin Cellulose [Stauber Performance Ingredients Inc.] | 27 mg |
| Microcrystalline Cellulose [FMC Corp.] | 190 mg |
| Di-Calcium phosphate [Brown Chemical Co. Inc.] | 82 mg |
| Magnesium Stearate [Stauber Performance Ingredients, Inc.] | 6.7 mg |
| Freeze dried alfalfa powder [Freeze-dry products USA, Inc.] | 18 mg |
| Freeze dried apple powder [Freeze-dry products USA, Inc.] | 17.2 mg |
| Freeze dried artichoke powder [Freeze-dry products USA, Inc.] | 16.5 mg |
| Freeze dried onion powder [Freeze-dry products USA, Inc.] | 19.6 mg |
| Freeze dried banana powder [Freeze-dry products USA, Inc.] | 6.3 mg |
| Freeze dried strawberry powder [Freeze-dry products USA, Inc.] | 14.1 mg |

-continued

| Ingredient | Approximate Amount |
|---|---|
| Freeze dried collard greens powder [Freeze-dry products USA, Inc.] | 7 mg |
| Freeze dried papaya powder [Freeze-dry products USA, Inc.] | 6 mg |
| Freeze dried green lettuce powder [Freeze-dry products USA, Inc.] | 6 mg |
| Freeze dried tomato powder [Freeze-dry products USA, Inc.] | 6 mg |
| Freeze dried broccoli powder [Freeze-dry products USA, Inc.] | 6 mg |
| Freeze dried cabbage powder [Freeze-dry products USA, Inc.] | 7 mg |
| Freeze dried cantaloupe powder [Freeze-dry products USA, Inc.] | 5 mg |
| Freeze dried cherry powder [Freeze-dry products USA, Inc.] | 5 mg |
| Freeze dried kale powder [Freeze-dry products USA, Inc.] | 10 mg |
| Freeze dried kiwi fruit powder [Freeze-dry products USA, Inc.] | 8 mg |
| Freeze dried kohlrabi powder [Freeze-dry products USA, Inc.] | 9 mg |
| Freeze dried grape powder [Freeze-dry products USA, Inc.] | 15 mg |
| Freeze dried grapefruit powder [Freeze-dry products USA, Inc.] | 11 mg |
| Freeze dried leek powder [Freeze-dry products USA, Inc.] | 11 mg |
| Freeze dried brussels sprout powder [Freeze-dry products USA, Inc.] | 11 mg |
| Freeze dried orange powder [Freeze-dry products USA, Inc.] | 13 mg |
| Freeze dried parsley powder [Freeze-dry products USA, Inc.] | 11 mg |
| Freeze dried potato powder [Freeze-dry products USA, Inc.] | 11 mg |
| Freeze dried bell pepper powder [Freeze-dry products USA, Inc.] | 12 mg |
| Freeze dried prune powder [Freeze-dry products USA, Inc.] | 6 mg |
| Freeze dried carrot powder [Freeze-dry products USA, Inc.] | 12 mg |
| Freeze dried Swiss chard powder [Freeze-dry products USA, Inc.] | 6 mg |
| Freeze dried spinach powder [Freeze-dry products USA, Inc.] | 18 mg |
| Freeze dried apricot powder [Freeze-dry products USA, Inc.] | 19 mg |
| Freeze dried avocado powder [Freeze-dry products USA, Inc.] | 15 mg |
| Freeze dried acorn squash powder [Freeze-dry products USA, Inc.] | 14 mg |
| Freeze dried savoy cabbage powder [Freeze-dry products USA, Inc.] | 8 mg |
| Freeze dried celery powder [Freeze-dry products USA, Inc.] | 5 mg |
| Freeze dried cauliflower powder [Freeze-dry products USA, Inc.] | 6 mg |
| Freeze dried sweet potato powder [Freeze-dry products USA, Inc.] | 7 mg |

*Fish oil is in the form of 300:200 of EPA:DHA.

Many modifications may be made without departing from the basic spirit of the present invention. Accordingly, it will be appreciated by those skilled in the art that within the scope of the appended claims, the invention may be practiced other than has been specifically described herein. Hence, the attached claims are intended to cover the invention embodied in the claims and substantial equivalents thereto.

We claim:

1. A nutritive composition comprising, as a daily dosage, lozenges for oral administration wherein the lozenges are comprised of:

approximately 500 mg to 15,000 mg fish oil, which comprises approximately 250 mg to 3500 mg EPA and approximately 150 mg to 2500 mg DHA, approximately 100 mg to 7,000 mg garlic powder, approximately 10 mg to 1,500 mg rutin, approximately 20 mg to 1,500 mg capsaicin, approximately 1,000 IU to 20,000 IU vitamin A, approximately 50 mg to 4,000 mg vitamin C, approximately 50 IU to 1,000 IU vitamin E, approximately 20 µg to 400 µg selenium, and approximately 1,000 mg to 7,500 mg of one or more juice concentrates having concentration of at least 10 times that of the native juice in unconcentrated form.

2. The nutritive composition of claim 1, wherein the juice concentrates are selected from the group consisting of acorn squash concentrate, alfalfa juice concentrate, apple juice concentrate, apricot juice concentrate, artichoke juice concentrate, avocado juice concentrate, banana juice concentrate, bell pepper juice concentrate, broccoli juice concentrate, brussels sprout juice concentrate, cabbage juice concentrate, cantaloupe juice concentrate, carrot juice concentrate, cauliflower juice concentrate, celery juice concentrate, cherry juice concentrate, collard greens juice concentrate, grape juice concentrate, grapefruit juice concentrate, green leek juice concentrate, green barley juice concentrate, green lettuce juice concentrate, kale juice concentrate, kiwi fruit juice concentrate, kohlrabi juice concentrate, leek juice concentrate, lettuce juice concentrate, onion juice concentrate, orange juice concentrate, papaya juice concentrate, parsley juice concentrate, potato juice concentrate, prune juice concentrate, savoy cabbage juice concentrate, spinach juice concentrate, strawberry juice concentrate, sweet potato juice concentrate, swiss chard juice concentrate, and tomato juice concentrate.

3. The nutritive composition of claim 1, wherein the garlic powder comprises a deodorized and aged form of garlic powder.

4. The nutritive composition of claim 1, wherein the selenium component is selected from the group consisting of organoselenium, selenium salt, and selenium-yeast.

5. The nutritive composition of claim 1, wherein the fish oil comprises EPA and DHA in a mass ratio of about 300:200.

6. The nutritive composition of claim 1, wherein the fish oil component of the nutritive composition is from about 5,000 mg to about 10,000 mg per daily dosage.

7. The nutritive composition of claim 5, wherein the fish oil component of the nutritive composition is from about 5,000 mg to about 10,000 mg per daily dosage.

8. The nutritive composition of claim 1, wherein the garlic powder component of the nutritive composition is from about 1,750 mg to about 6,500 mg per daily dosage.

9. The nutritive composition of claim 1, wherein the garlic powder component of the nutritive composition is about 3,500 mg per daily dosage.

10. The nutritive composition of claim 1, wherein the rutin component of the nutritive composition is about 1,000 mg per daily dosage.

11. The nutritive composition of claim 1, wherein the capsaicin component of the nutritive composition is about 1,000 mg per daily dosage.

12. The nutritive composition of claim 1, wherein the vitamin A component of the nutritive composition is about 2,000 IU to about 15,000 IU per daily dosage.

13. The nutritive composition of claim 1, wherein the vitamin A component of the nutritive composition is about 2,500 IU to about 10,000 IU per daily dosage.

14. The nutritive composition of claim 1, wherein the vitamin C component of the nutritive composition is about 150 mg to about 3,000 mg per daily dosage.

15. The nutritive composition of claim 1, wherein the vitamin C component of the nutritive composition is about 175 mg to about 2,000 mg per daily dosage.

16. The nutritive composition of claim 1, wherein the vitamin E component of the nutritive composition is about 75 IU to about 925 IU per daily dosage.

17. The nutritive composition of claim 1, wherein the vitamin E component of the nutritive composition is about 125 IU to about 425 IU per daily dosage.

18. The nutritive composition of claim 1, wherein the selenium component of the nutritive composition is about 55 µg to about 300 µg per daily dosage.

19. The nutritive composition of claim 1, wherein the selenium component of the nutritive composition is about 150 µg to about 250 µg per daily dosage.

20. The nutritive composition of claim 1, wherein the juice concentrates component of the nutritive composition is about 2,000 mg to about 6,000 mg per daily dosage.

21. The nutritive composition of claim 1, wherein the nutritive composition further comprises a suitable pharmaceutical carrier for administration, wherein the suitable carrier comprises more or more excipients selected from the group consisting of: starches, sugars, diluents, granulating agents, lubricants, and binders.

22. The nutritive composition of claim 1, wherein the nutritive composition further contains one or more inert ingredients selected from the group consisting of: lemon bioflavonoids, parsley powder, bee's wax, lecithin, gelatin, purified water, and glycerin.

* * * * *